United States Patent
Lo et al.

(10) Patent No.: US 9,451,898 B2
(45) Date of Patent: Sep. 27, 2016

(54) METHOD AND SYSTEM FOR EXTRACTING VENTRICULAR FIBRILLATION SIGNALS IN ELECTROCARDIOGRAM USING SPLINE INTERPOLATION WITH UNIFORM PHASE ENSEMBLES

(71) Applicant: National Central University, Taoyuan (TW)

(72) Inventors: Men-Tzung Lo, Taoyuan (TW); Yung-Hung Wang, Taoyuan (TW); Chen Lin, Taoyuan (TW); Hsu-Wen Vincent Young, Taoyuan (TW); Hsiang-Chih Chang, Taoyuan (TW); Lian-Yu Lin, Taipei (TW); Wan-Hsin Hsieh, Taoyuan (TW); Matthew Huei-Ming Ma, Taipei (TW); Kun Hu, Taoyuan (TW)

(73) Assignee: NATIONAL CENTRAL UNIVERSITY, Taoyuan (TW)

( * ) Notice: Subject to any disclaimer, the term of this patent is extended or adjusted under 35 U.S.C. 154(b) by 0 days.

(21) Appl. No.: 14/993,584

(22) Filed: Jan. 12, 2016

(65) Prior Publication Data
US 2016/0120429 A1    May 5, 2016

Related U.S. Application Data

(63) Continuation-in-part of application No. 14/322,497, filed on Jul. 2, 2014, now Pat. No. 9,259,167.

(51) Int. Cl.
| | |
|---|---|
| *A61B 5/04* | (2006.01) |
| *A61B 5/046* | (2006.01) |
| *A61B 5/00* | (2006.01) |
| *A61B 5/11* | (2006.01) |

(52) U.S. Cl.
CPC ........... *A61B 5/046* (2013.01); *A61B 5/04012* (2013.01); *A61B 5/04014* (2013.01); *A61B 5/7207* (2013.01); *A61B 5/11* (2013.01)

(58) Field of Classification Search
CPC .......... A61B 5/04012; A61B 5/04014; A61B 5/046; A61B 5/11; A61B 5/7207
See application file for complete search history.

(56) References Cited

U.S. PATENT DOCUMENTS

| | | | |
|---|---|---|---|
| 2008/0183093 A1* | 7/2008 | Duann | A61B 5/04525 600/516 |
| 2010/0195770 A1* | 8/2010 | Ricci | G06K 9/00523 375/322 |
| 2014/0100466 A1 | 4/2014 | Hayashi et al. | |

OTHER PUBLICATIONS

Lo, Men-Tzung et al., A new method to estimate the amplitude spectrum analysis of ventricular fibrillation during cardiopulmonary resuscitation, Resuscitation, 2013, vol. 84, pp. 1505-1511.

*Primary Examiner* — George Manuel
(74) *Attorney, Agent, or Firm* — Muncy, Geissler, Olds & Lowe, P.C.

(57) ABSTRACT

This invention discloses a system and a method for extracting VF signal in ECG recorded during uninterrupted CPR. The present invention provides a method for extracting a Ventricular fibrillation (VF) signal in Electrocardiography (ECG), comprising: receiving an ECG signal; adding a plurality of shadowing functions to the ECG signal, to obtain a plurality of modification signals; decomposing the plurality of modification signals by using an Empirical Mode Decomposition (EMD) method, to generate a plurality of Intrinsic Mode Functions (IMFs); calculating the sum of IMFs in different frequency regions based on time sequence, dividing by a number of the shadowing signal, to obtain a plurality of modification intrinsic mode functions; combining the plurality of modification IMFs with the same property, to obtain a shape function; modeling the shape functions to obtain a compression signal; and subtracting the compression signal from the ECG signal based on time sequence, to obtain the VF signal.

10 Claims, 9 Drawing Sheets

METHOD AND SYSTEM FOR EXTRACTING VENTRICULAR FIBRILLATION SIGNALS IN ELECTROCARDIOGRAM USING SPLINE INTERPOLATION WITH UNIFORM PHASE ENSEMBLES

CROSS-REFERENCE TO RELATED APPLICATIONS

This application is a continuation-in-part of U.S. patent application Ser. No. 14/322,497 filed on Jul. 2, 2014. This application claims benefit to these earlier filed applications under 35 U.S.C. §120. The entire contents of all earlier filed applications are hereby incorporated by reference.

FIELD OF THE INVENTION

The invention relates to a method and a system for extracting ventricular fibrillation (VF) signals, more particularly, to the method and the system for extracting ventricular fibrillation (VF) signals in electrocardiogram (ECG) recorded during uninterrupted Cardio Pulmonary Resuscitation (CPR).

BACKGROUND OF THE INVENTION

Ventricular fibrillation is the most common etiology leading to sudden cardiac death. Early defibrillation and non-interrupted Cardio Pulmonary Resuscitation are the most important determinants for restoration of spontaneous circulation in patients with VF. The occurrence of VF out of hospital makes early defibrillation hard to be realized. Fortunately, the VF waveform analysis such as amplitude spectrum analysis (AMSA) could help estimate the duration of VF, determine the shock ability by assessing the VF waveform as being fine or coarse, and predict the probability of successful defibrillation, and has been applied to the conventional Automatic External Defibrillator (AED) for providing early defibrillation during the occurrence of VF out of hospital.

Although studies have demonstrated interruption of CPR greatly decreases the probability of successful resuscitation, non-interrupted CPR during recording Electrocardiography (ECG) for the VF waveform analysis is still a challenge. Empirical mode decomposition (EMD) is a signal analysis method which has received much attention lately due to its application in a number of fields. The problem of mode mixing in Empirical Mode Decomposition is caused by the intermittency signals and noises, which is defined as a single Intrinsic Mode Function (IMF) consisting of signals of widely disparate scales. The mode mixing of EMD is caused by the input data consisting of intermittent oscillations of two or multi scales, a low frequency component and another higher frequency component occurring only at some part of the signal. In this situation, the sifting process detects the extrema of higher frequency component in some parts of the signal and detects the extrema of low frequency component for other parts of the signal. Then the locations of extrema are highly non-uniformly distributed and the extrema detected in the sifting process belong to different signals, therefore the decomposed IMF will contain mixed modes.

Suppose a signal consists of many tones with frequencies. A tone is distributed into many IMFs after the decomposition. The IMF contains the most energy of tone is designated as the major component of the tone and other IMFs are designated as the minor component of the tone. Then the mode splitting effect is defined as the leakage of the tone into other IMFs with indices.

The mode splitting effect is a natural consequence of EMD and its degree can be measured. The frequency ratio of the low frequency to higher frequency component or extrema (distribution) rate ratio is the source for producing mode splitting. As the extrema rate ratio is closer to one, then the mode splitting become more severe.

SUMMARY OF THE INVENTION

The present invention discloses a method and a system for extracting a VF signal in ECG The method and the system applies a conjugate function to a non-linear and non-stationary signal for correcting a value of particular frequency function, then calculating the sum of IMFs and dividing by a number of the shadowing signal to resolve the problems of mode mixing and mode splitting.

The present invention provides a system for extracting a VF signal in ECG, comprising a signal collecting unit, a signal processing unit and a signal outputting unit. The signal collecting unit is for receiving an ECG signal.

The signal processing unit is electrically connected to the signal collecting unit for adding a plurality of shadowing functions to the ECG signal, to obtain a plurality of modification signals, wherein each pair of shadowing functions is conjugate and has same phase difference, decomposing the plurality of modification signals by using an Empirical Mode Decomposition (EMD) method, to generate a plurality of Intrinsic Mode Functions (IMFs), calculating the sum of IMFs in different frequency regions based on time sequence, dividing by a number of the shadowing signal, to obtain a plurality of modification intrinsic mode functions, combining the plurality of modification IMFs with the same property, to obtain a shape function, modeling the shape functions to obtain a compression signal, and subtracting the compression signal from the ECG signal based on time sequence, to obtain the VF signal.

The signal outputting unit is connected to the signal processing unit to output the VF signal.

In an embodiment of the invention, the present invention provides a method for extracting a Ventricular Fibrillation (VF) signal in Electrocardiography (ECG), comprising: receiving an ECG signal; adding a plurality of shadowing functions to the ECG signal, to obtain a plurality of modification signals, wherein each pair of shadowing functions is conjugate and has same phase difference; decomposing the plurality of modification signals by using an Empirical Mode Decomposition (EMD) method, to generate a plurality of Intrinsic Mode Functions (IMFs); calculating the sum of IMFs in different frequency regions based on time sequence, dividing by a number of the shadowing signal, to obtain a plurality of modification intrinsic mode functions; combining the plurality of modification IMFs with the same property, to obtain a shape function; modeling the shape functions, to obtain a compression signal; and subtracting the compression signal from the ECG signal based on time sequence, to obtain the VF signal.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the FIG. 1 is a block diagram of a system of signal processing.

DETAILED DESCRIPTION OF THE INVENTION

Summering various aspects of the present disclosure, reference will now be made in detail to the description of the disclosure as illustrated in the drawings. While the disclosure will be described in connection with these drawings, there is no intent to limit it to the embodiments disclosed herein. On the contrary, the intent is to cover all alternatives, modifications and equivalents included within the spirit and scope of the disclosure as defined by the appended claims.

The present invention discloses a method implemented in a data analysis system for extracting a Ventricular Fibrillation signal in Electrocardiography. It is understood that the method provides merely an example of the many different types of functional arraignments that may be employed to implement the operation of the various components for extracting a ventricular fibrillation signal in electrocardiography, a computer system connected to a scanner, a multiprocessor computing device, and so forth. The execution steps of the present invention may include application specific software which may store in any portion or component of the memory including, for example, random access memory (RAM), read-only memory (ROM), hard drive, solid-state drive, magneto optical (MO), IC chip, USB flash drive, memory card, optical disc such as compact disc (CD) or digital versatile disc (DVD), floppy disk, magnetic tape, or other memory components.

For an embodiment, the system comprises a display device, a processing unit, a memory, an input device and a storage medium. The input device used to provide data, such as image, text or control signals, to an information processing system, such as a computer or other information appliance.

In accordance with some embodiments, the storage medium, such as a hard drive, an optical device or a remote database server, coupled to a network, and stores software programs. The memory typically is the process in which information is encoded, stored, and retrieved etc. The processing unit performs data calculations, data comparisons, and data copying. The display device is an output device that visually conveys text, graphics, and the VF signal. Information shown on the display device is called soft copy because the information exists electronically and is displayed for a temporary period of time. The display device includes CRT monitors, LCD monitors and displays, gas plasma monitors, and televisions.

In accordance with such embodiments of present invention, the software programs are stored in the memory and executed by the processing unit when the computer system executes the method for extracting a ventricular fibrillation signal in electrocardiography. Finally, information provided by the processing unit, and presented on the display device or stored in the storage medium.

Figure 1:
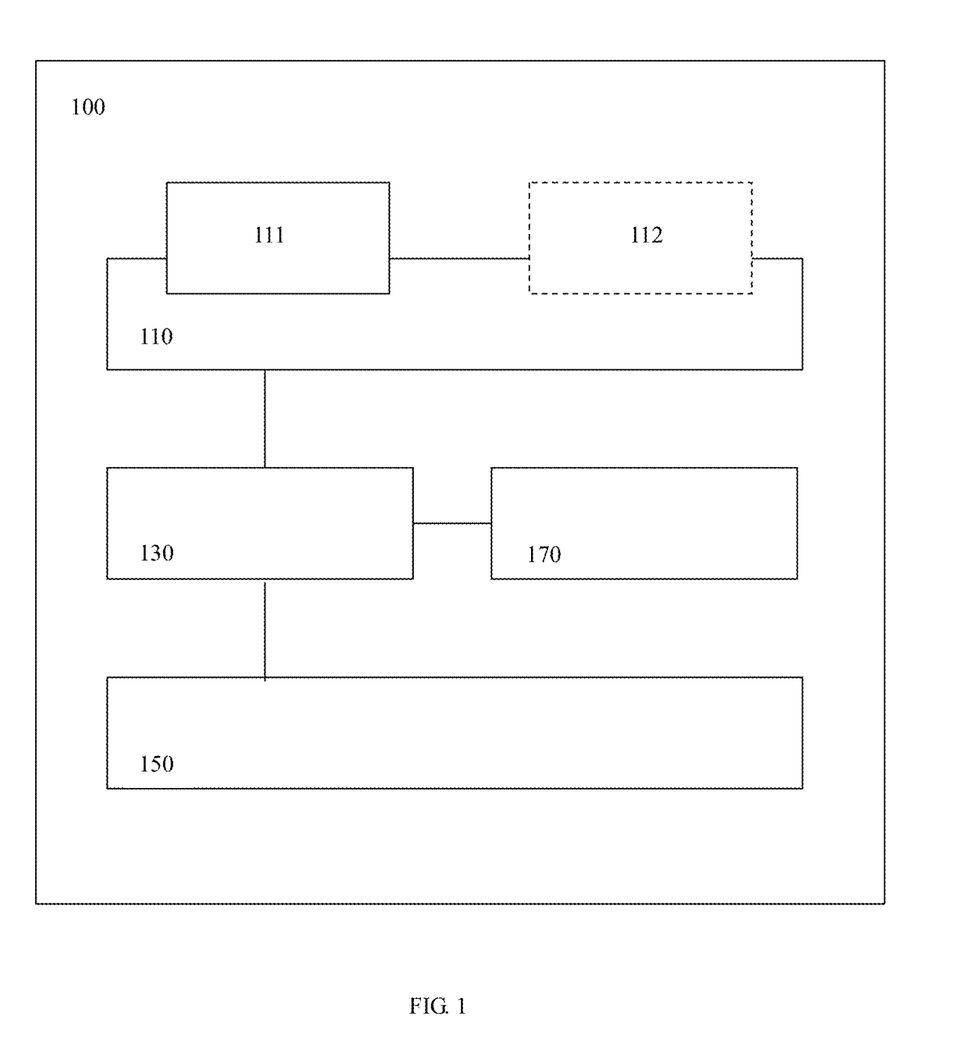
Figure 2:
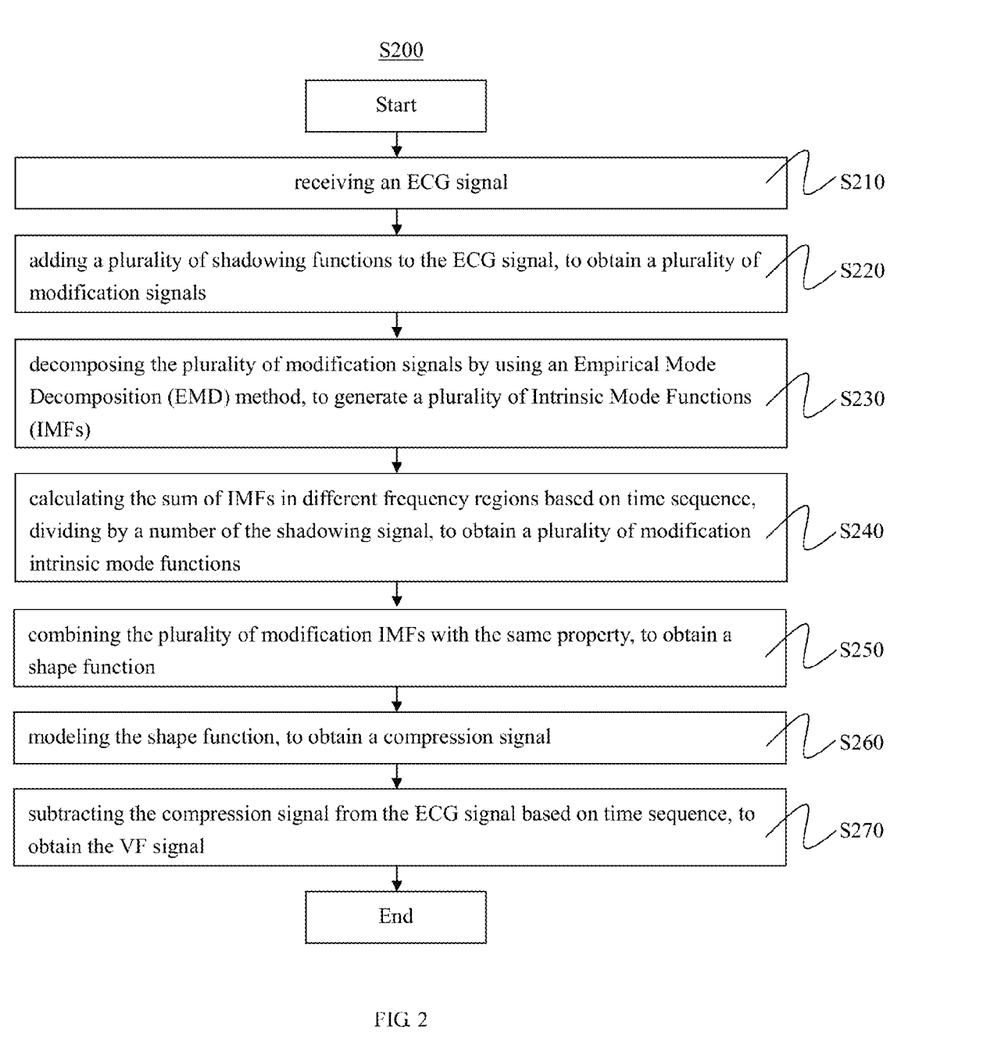
FIG. 2 is a exemplary steps flowchart of a signal processing method for phase-amplitude coupling.

FIG. 1 and FIG. 2 respectively show a system 100 and a method S200 for extracting a ventricular fibrillation signal in ECG according to an embodiment of the present invention. A method S200 for extracting a ventricular fibrillation signal in electrocardiography may be implemented in the system 100. The system 100 includes a signal collecting unit 110, a signal processing unit 130, and a signal outputting unit 150. The signal collecting unit 110 is electrically connected to the signal processing unit 130. Meanwhile, the signal processing unit 30 is electrically connected to the signal outputting unit 150.

In another embodiment, as shown in FIG. 1, the signal collecting unit 10 may include an ECG port 111 and a reference signal port 112. The signal collecting unit 10 may receive a reference signal which is related to the chest compressions variation of CPR through the reference signal port 112. An inexpensive accelerometer, such as a wrist accelerometer, measures the reference signal according to the acceleration generated from the chest compression movement during CPR. Preferably, the reference signal may be a function of amplitude and time.

The method S200 and the system 100 can be applied on a mobile phone, an AED, a notebook, or a computer, which is not limited herein. The method S200 for extracting a VF signal in ECG includes the steps of: receiving an ECG signal (step S210); adding a plurality of shadowing functions (sinusoid) to the ECG signal, to obtain a plurality of modification signals, wherein each pair of shadowing functions is conjugate and has same phase difference (step S220); decomposing the plurality of modification signals by using an Empirical Mode Decomposition (EMD) method, to generate a plurality of Intrinsic Mode Functions (IMFs) (step S230), wherein each of the IMFs is an expression equivalent of the received signal; calculating the sum of IMFs in different frequency regions based on time sequence, dividing by a number of the shadowing signal, to obtain a plurality of modification intrinsic mode functions (step S240);combining the plurality of modification IMFs with the same property, to obtain a shape function (step S250); and identifying each cycle (the cycle can be defining, such as a cycle of each chest compression action), modeling each cycle of the shape function, to obtain a compression signal (step S260). In an example, it may uses the Least Mean Square (LMS) method to obtain the compression signal ; and subtracting the compression signal from the ECG signal to obtain the VF signal (step S270).

Firstly, the signal collecting unit 10 receives an ECG signal (step S210) through an ECG port 111.

In another embodiment, the signal collecting unit 110 may receive the ECG signal wirelessly. The ECG signal may be recorded from a patient with VF or suspected VF without stopping the CPR procedure, so that the recorded ECG signal carries some chest compression related signals which may affect the following VF waveform analysis for determining the shock ability, wherein the ECG signal is a function of amplitude and time.

A signal processing unit 130 adds a plurality of shadowing functions (sinusoids) to the ECG signal to obtain a plurality of modification signals, wherein each pair of shadowing functions has same phase difference (step S220). The signal processing unit 130 decomposes the plurality of modification signals by using an empirical mode decomposition method to generate a plurality of intrinsic mode functions (step S230), wherein each of the IMFs is an expression equivalent of the received signal.

For an embodiment, the function of the shadowing signal (sinusoid) is calculated according to the following expression:

$$w_i(t)=\epsilon^* \cos(2\pi t/T_w - 2\pi i/np)$$

wherein $t \in N$ and $t=1,2,3,\ldots$, $\epsilon$ is the amplitude of the shadowing function; $T_w$ is a period of the shadowing signal, np is the number of the shadowing signal, and i is the index ranges from 1 to np.

Figure 3:
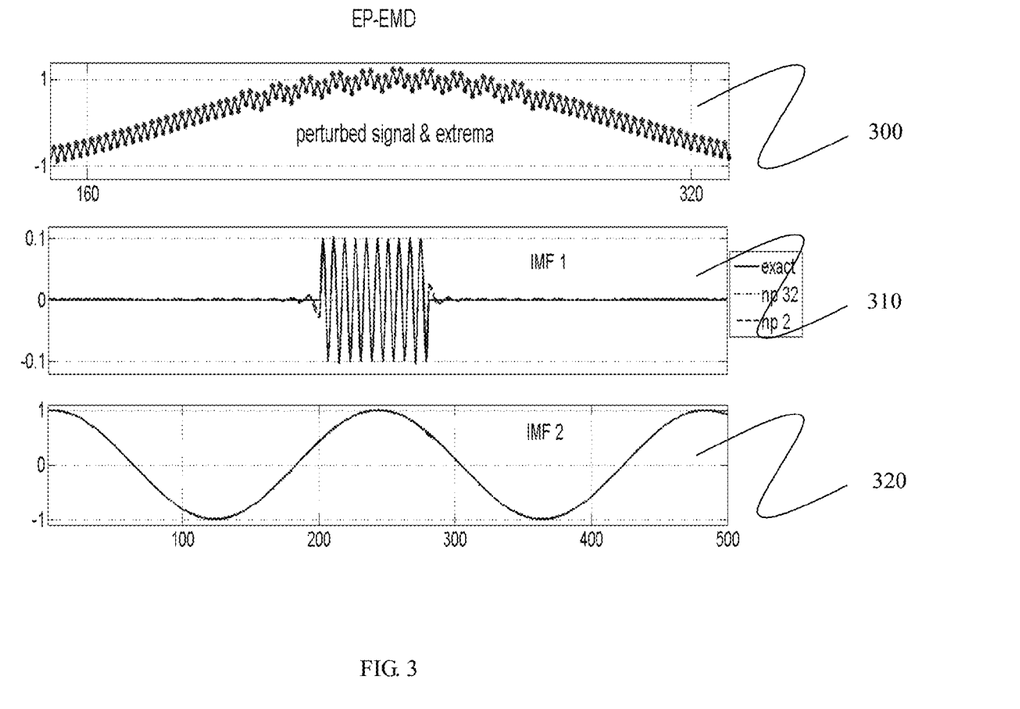
FIG. 3 illustrates two scale UPEMD-32 (np=32) and UPEMD-2 (np=2).

Please refer FIG. 3, FIG. 3 illustrates two scale UPEMD-32 (np 32) and UPEMD-2 (np 2). The signal processing unit 130 adds a first shadowing signal (sinusoid) to a perturbed signal 300, for example, two tone signal to obtain a first modification signal, and generates a plurality of first intrinsic mode functions by using the EMD method, wherein the first intrinsic mode function is an expression amplitude of the first modification signal in the frequency region.

And the signal processing unit 130 adds a second shadowing signal to the ECG signal, to obtain a second modification signal, and generates a plurality of second intrinsic mode functions by using the EMD method, wherein the second intrinsic mode function is an expression amplitude of the second modification signal in the frequency region. The first shadowing function and the second shadowing function are conjugated.

Then, the signal processing unit 130 repeats to add a np-1 shadowing signal and a np shadowing signal to the ECG signal to obtain the plurality of intrinsic mode functions, wherein the phase difference of the shadowing signals are constant.

The signal processing unit 130 selects the intrinsic mode functions corresponding to a first frequency region, calculates the sum of the intrinsic mode functions based on the time sequence, then dividing by the number of shadowing signal, to obtain a first modification intrinsic mode function 310, and selects the intrinsic mode functions corresponding to a second frequency region (step S240), calculates the sum of the intrinsic mode functions based on the time sequence, then dividing by the number of shadowing signal, to obtain a second modification intrinsic mode function 320 (step S240).

Then, the signal processing unit 30 selects the intrinsic mode functions corresponding to different frequency region repeatedly until to obtain the modification intrinsic mode functions from all frequency regions.

In FIG. 3, the present invention provides the method aiming at separating the two tone signal 310, 320.

The number of the shadowing signal is noted as np, where $np \in N$ and $np \geq 2$, and the phases, $\theta_k$, are uniformly distributed over the $2\pi$ space. Then the phase $\theta_k$ is determined as $\theta_k = 2\pi(k-1)/np$, $k=1:np$.

Then, the algorithm is the referred as the two-scale uniform phase EMD (UPEMD) with phase number np and is noted as UPEMD-np. For an example, if np=16, it is noted as UPEMD-16. The special case when the number of the shadowing signal is equal to the period of the shadowing signal, i.e., $np=T_w$, the algorithm is the referred as the UPEMD with ensemble phase, and is noted as UPEMD-ensemble. The present method is applied to decompose the example of the two tone signal with intermittency. The frequency of the shadowing signal is chosen to be identical to that of the higher frequency component. The phase $\phi$ are arbitrarily chosen and he amplitude $\epsilon$ is chosen from the range 0 to $\infty$.

Assuming each IMF is stationary and each tone $p_j(t)$ is leaked into all IMFs, then each IMF contains a fragment of tone, $p_j(t)$, i.e., $\alpha_{j,m} p_j(t)$, where $\alpha_{j,m}$ is the attenuation ratio of the jth tone onto IMF m.

$$\Sigma_{m=1}^{mimf} \alpha_{j,m}=1=1:n_c.$$

An IMF, $c_m$, is contaminated by the residual noise $\epsilon_{res,m}$ $$c_m(t) = \sum_{j=1}^{n_o} \alpha_{j,m} p_j(t) + \varepsilon_{res,m}$$

The equation states that each IMF can be written as the summation over the attenuated copy of each tone plus the residual noise $\epsilon_{res,m}(t)$. Larger $\|\epsilon_{res,m}(t)\|$ implies more severe residual noise effect and vice versa. The mode splitting index is used to quantify the mode splitting effect, which is defined as the percentage of the leakage of the amplitude of tone j into other IMFs, that is $$MSI_j=1-\max_m(\alpha_{j,m})/\Sigma_{m-1}^{mimf}\alpha_{j,m}=1-\max_m(\alpha_{j,m}).$$

The two-tone signal is given by $$y_k(t)=\alpha_{HF} \cos(2\pi f_{HF} t + \phi_{HF}) + \alpha_{LF} \cos(2\pi f_{LF} t + \Phi_L F),$$

where the subscript HF and LF denotes the shadowing function and the low frequency component, respectively. Define the frequency ratio $$\tilde{f} \stackrel{\Delta}{=} f_{LF}/f_{HF} < 1$$

and the amplitude ratio $$\tilde{a} \stackrel{\Delta}{=} a_{LF}/a_{HF}.$$

Figure 5:
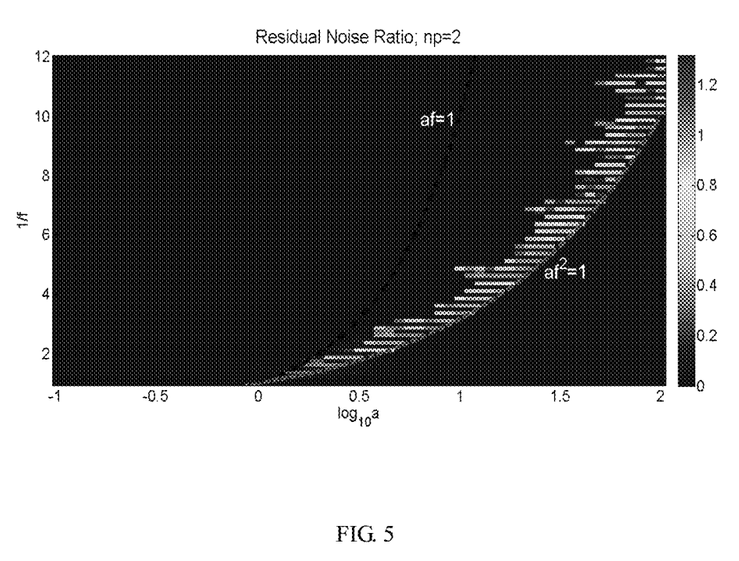
FIGS. 5 and 6 illustrates the residual noise decomposed by UPEMD-16 (np=16) and UPEMD-2 (np=2).
Figure 6:
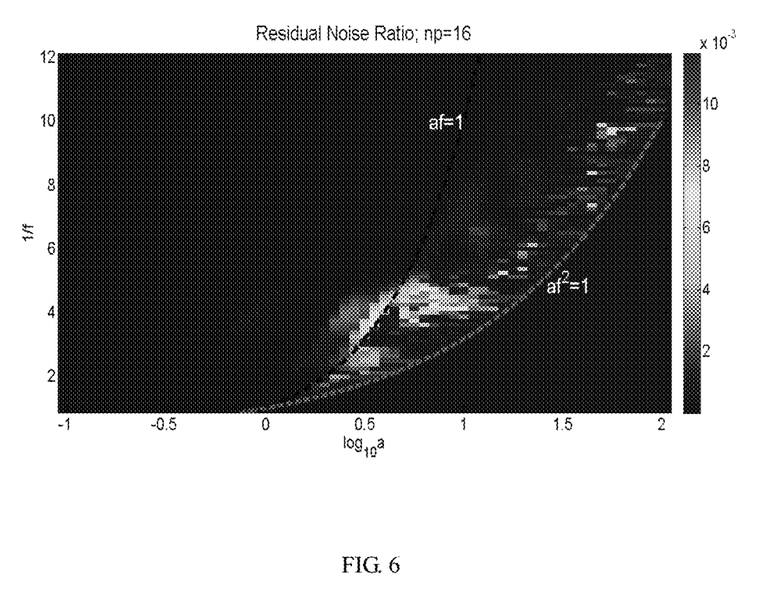

The FIGS. 5 and 6 can be categorized into 3 regions. (A). $\tilde{a}\tilde{f}^2>1$; (B). $\tilde{a}\tilde{f}<1$; (C). $\tilde{a}\tilde{f}\geq 1$ & $\tilde{a}\tilde{f}^2\leq 1$. Mode splitting occurs in region (B) and (C), but does not in region (A). The residual noise mainly occurs in region (C). Recall that the perturbed signal consists of an assisted shadowing function (sinusoid) plus the lower frequency tone, which is also a shadowing function with different frequency. Therefore the decomposition of the one tone signal by UPEMD is equivalent to the decomposition of two tone signal by EMD.

FIG. 3 also shows that the present invention resolves the mode mixing and produces no significant mode splitting. Although assisted the shadowing function is stationary, the shadowing function serves as a media to assist the extraction of the scales similar to the mask, it would not lose the ability of decompose nonlinear and non-stationary signal.

Figure 4A:
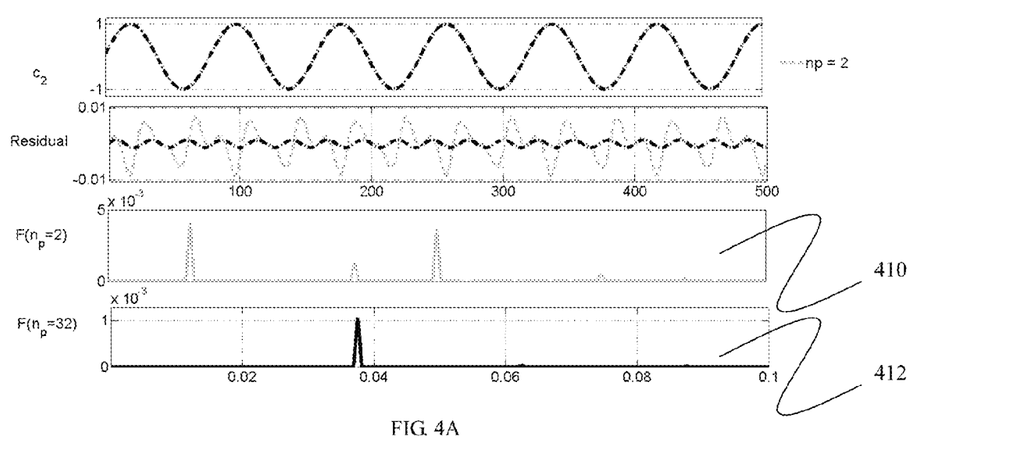
FIG. 4A illustrates the Fourier spectrums for intrinsic mode functions.

Please refer FIG. 4A, FIG. 4A illustrates the Fourier spectrums for intrinsic mode function. The waveforms are examined for the first modification intrinsic mode function by taking the parameters $\tilde{f}\approx 0.4$ Hz, $f_{HF}=1/32$ and $\tilde{a}=2$ such that $\tilde{a}\tilde{f}\approx 0.8$. The Fourier spectrums 410-412 are corresponding to UPEMD-2 ($n_p=2$) and UPEMD-32 ($n_p=32$) respectively. The mode splitting index are 0.41% and 0.42% for UPEMD-2 and UPEMD-32 respectively, which shows the mode splitting are insensitive to the phase number. The mode splitting index is about $2 \cdot 10^{-6}$%. The maximum residual noise $\epsilon_{res}$ are 0.88% and 0.1% for the 2-phase and 32-phase respectively, which demonstrates that the residual noise is significant improved by the UPEMD-32 because the more of the higher order term of the residual noise is cancelled out for the 32 phases algorithm than that of the 2 phases algorithm.

Figure 4B:
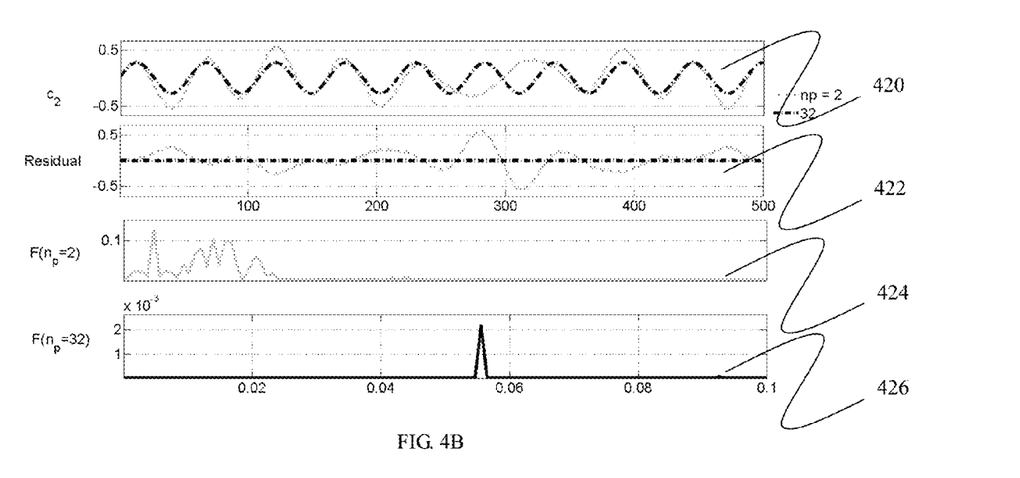
FIG. 4B illustrates the decomposition by UPEMD-32 ($n_p$=32) and UPEMD-2 ($n_p$=2) method.

FIG. 4B illustrates the results of the decomposition by UPEMD-2 ($n_p$=2) and UPEMD-32 ($n_p$=32). The results with parameters $\tilde{f}$≅0.59 Hz, $f_{HF}$=1/32 and $\tilde{a}$=2 such that $\tilde{a}\tilde{f}$≅1.2 and $\tilde{a}\tilde{f}^{2b}$ ≅0.7. The perturbed signal by the first realization is presented in the top panel 420 in FIG. 4B and the decomposition of the perturbed signal by EMD are presented in the $2^{nd}$ panel 424 and $3^{rd}$ panel 426 in FIG. 4B. In the first panel 422 of FIG. 4B, in this region the extrema rate is not uniform and the amplitude of the assisted shadowing function (sinusoid) is smaller than that of the tone, then the EMD interprets the perturbed signal with intermittency which can be also confirmed by the decomposed IMFs shown in FIG. 4B. The results of the decomposition by UPEMD-2 and UPEMD-32 are presented in FIG. 4B. The MSI are 30% and 27% respectively which demonstrates the mode splitting effect is insensitive to the phase number. The maximum residual noise $\epsilon_{res}$ are 58% and 0.2% for the 2-phase and 32-phase respectively.

FIGS. 5 and 6 illustrates the residual noise decomposed by the UPEMD-2 (np=2) and UPEMD-16 (np=16) method. FIGS. 5 and 6 express the residual noise versus different combinations of signal amplitude ($\log_{10}a$) and frequency (1/f). The residual noise for the UPEMD-16 method in FIG. 6 is significantly reduced compared to that of the UPEMD-2 in FIG. 5. The maximum residual noises are about 120% and 1% for the 2 and the 16 phases method respectively, which demonstrates that the residual noise is significant improved by the UPEMD with more phases.

The real-world data often consists of multi-scale information. The key to the multi-scale UPEMD is to add the shadowing function (sinusoid) at each level of IMF extraction stage recursively from smaller time scale to longer time scale and each of the extracted IMF will be perfected reconstructed. The determination of the frequency and amplitude of the assisted shadowing function is based by the following rules. For frequency, the EMD acts as an adaptive dyadic filter bank for the decomposition of the white noise. The present invention provides number of IMF $n_{imf}$ is taken approximately as $n_{imf}$=$\log_2 n$. Therefore a natural choice of the period of the assisted shadowing function for IMF m is $T_w$=$2^m$ for m=1:$\log_2 n$.

The present invention applies the multi-scale UPEMD to decompose the example of two tone signal with intermittency. The input signal is previously performed by the two-scale UPEMD, in which we assume the time scales of the input signal is already known.

In an embodiment, the signal processing unit 30 adds a first-level of first shadowing signal to the ECG signal, to obtain a first-level of first modification signal, and generates a plurality of first-level of first intrinsic mode functions by using the EMD method, wherein the first-level of first intrinsic mode function is an expression amplitude of the first-level of first modification signal in the first frequency region.

And adds a first-level of second shadowing signal to the ECG signal to obtain a first-level of second modification signal, and generates a plurality of first-level of second intrinsic mode functions by using the EMD method, wherein the first-level of second intrinsic mode function is an expression amplitude of the first-level of second modification signal in the first frequency region.

Then adds a first level of np-1 shadowing signal and a first level of np shadowing signal to the ECG signal repeatedly, to obtain the plurality of first level intrinsic mode functions, wherein the phase difference of the shadowing signals are constant.

The signal processing unit 130 further calculates the sum of the first level intrinsic mode functions based on the time sequence, divides by the number of shadowing signal, to obtain a first modification intrinsic mode function, and adds a m level of shadowing signal to the ECG signal repeatedly, to obtain a plurality of m level of intrinsic mode functions.

Then calculates the sum of m level of the intrinsic mode functions based on the time sequence, divides by the number of shadowing signal, to obtain a first level of m modification intrinsic mode function, until to obtain the modification intrinsic mode functions from all frequency regions.

For an embodiment, the function of the shadowing signal is calculated according to the following expression:

$$w_i(t)=\epsilon * \cos(2\pi t/2^m - 2\pi i/np)$$

wherein the np-1 shadowing signal and the np shadowing signal is a m level of the shadowing function and m is corresponding to the m level of the modification intrinsic mode function.

Figure 7A:
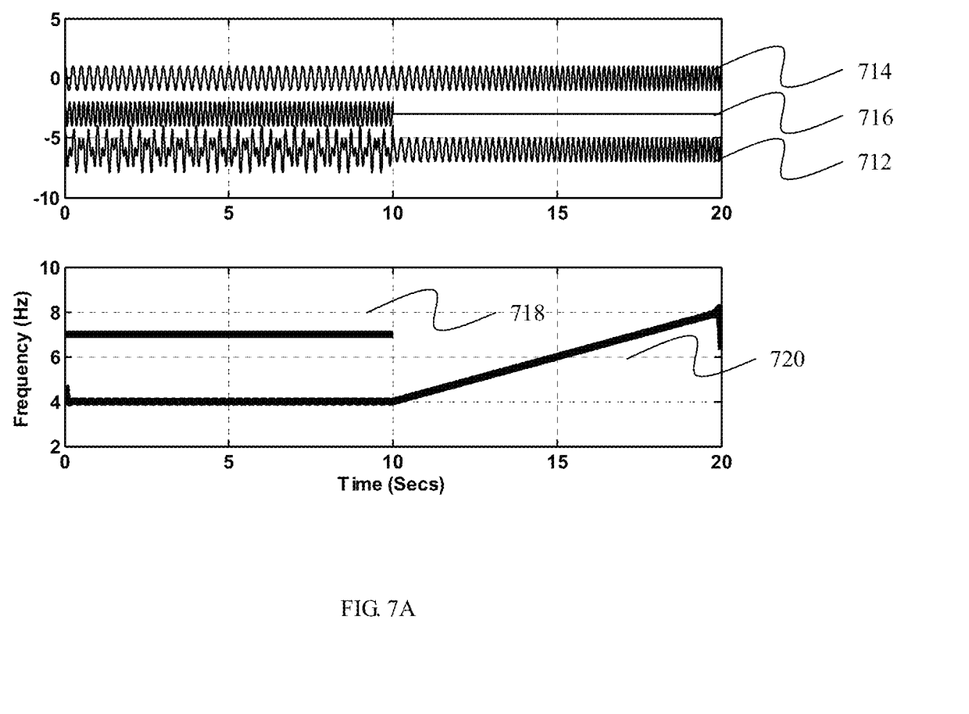
FIG. 7A illustrates a signal changing over time.
Figure 7B:
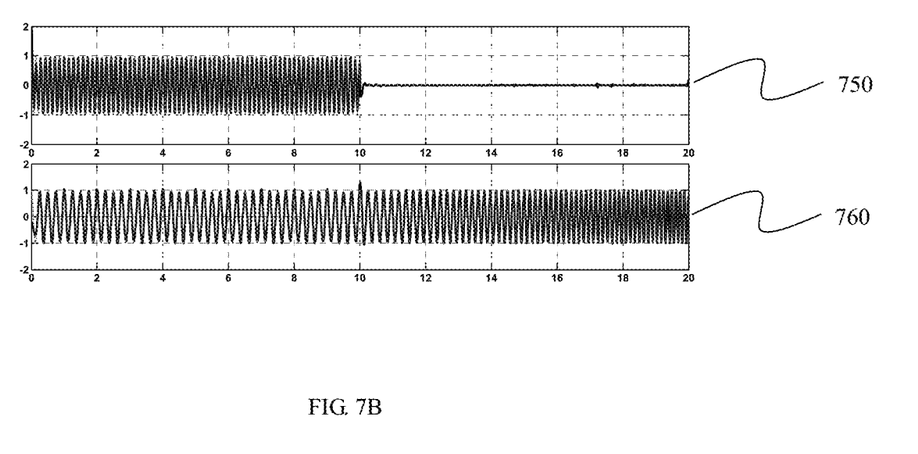
FIG. 7B illustrates the signals filtered by the adaptive masking method.

Please refer FIG. 7A and 7B, FIG. 7A illustrates a signal changing over time, and FIG. 7B is a schematic diagram showing the signals filtered by the adaptive masking. The real-world data often a collected signal comprises at least two signals, wherein the frequency of signal changes over time. FIG. 7A is a schematic diagram showing a signal consists of many tones with frequencies.

The S signal 712 comprises a S1 signal 714 and S2 signal 716. The S1 signal has stationary frequency 720 (f1) in 4 Hz at first ten second, the frequency (f1) increases from ten to twenty second. The S2 signal is only ten second with frequency 718 (f2) in 7 Hz. However, the S signal cannot be effective filtered by using a filter with a specified frequency or a single masking frequency (fm) for masking. Therefore, an adaptive masking is generated based on a function of masking frequency changes over time to filter S1 signal 714 and S2 signal 716. In FIG. 7B, the S1 signal 750 and S2 signal 760 is filtered by the adaptive masking method effectively.

The signal processing unit 30 combines the plurality of IMFs with the same property to obtain a shape function (step S250). In this step, some IMFs features the compression signal should be chosen. Generally, the signal strength of the compression signal is prominently larger than that of the VF signal. That's why we considered the main fluctuations of ECG signal are from the compression signal. Some IMFs featuring the compression signal may have the same property with the ECG signal. As a result, calculates the correlation coefficient of each IMF and the ECG signal, and then selecting some of IMFs with higher correlation coefficient than others. Combining the IMFs may obtain a shape function which almost reconstructs the fluctuation of the compression signal.

The time interval for each chest compression can be easily identified and correctly estimated from the shape function reconstructed by EMD/EEMD. The rate of each compression was then determined by the inverse of the compression cycle lengths.

After identifying the rates of chest compressions, the signal processing unit 30 models the shape function using the Least Mean Square (LMS) to obtain a compression signal (step S260). The shape function is further refined through step S260. The LMS model hypothesizes that each chest compression signal (each cycle of shape function) is composed of K harmonics of the sinusoids with variable period determined by the EMD derived the shape function. Therefore, the chest compression signal with time varying compression rates was further elaborated by LMS model as provided by $$\hat{S}_{CPR}(t) = \sum_{k=1}^{K} A_k(n)\cos(2\pi k f_0(n)t/f_s + \theta_k(t))$$

$$= \sum_{k=1}^{K} a_k(n, t)\cos(2\pi k f_0(n)t/f_s) +$$

$$b_k(n, t)\sin(2\pi k f_0(n)t/f_s)$$

$$= \sum_{k=1}^{K} a_k(n, t)\cos(k\phi(n, t)) +$$

$$b_k(n, t)\sin(k\phi(n, t))$$

where $f_0(n)$ was the time-varying frequency of n-th compression, $f_s$ was the sampling rate, $\theta_k(t)$ denoted the time-varying phase corresponding to k-th harmonic signal, and $a_k(n,t)$ and $b_k(n,t)$ were the $\phi(n,t)=2\pi f_0(n)t/f_s$ time-varying in-phase and quadrature coefficients of the filter for n-th compression. The Equation may be the LMS-refined shape function, and may be stored in the storage unit 170 in advance for the simplified process.

Note that the time-varying frequency $f^0(n)$ was obtained by the inverse of cycle length of n-th compression in the shape function. For modeling compressions cycle by cycle, the Equation could be simplified by $$\hat{S}_{CPR}(t) = \sum_{k=1}^{K} a_k(t)\cos(k\phi(t)) + b_k(t)\sin(k\phi(t))$$

In each compression cycle, $a_k(t)$ and $b_k(t)$ would be trained and repeatedly updated according to the difference between ECG signal and modeled shape function in LMS algorithm. Let a(t) and b(t) be the column vectors of the in-phase and the quadrature filter coefficients at time k in two column vectors, namely $$a(t)=[a_1(t), \ldots, a_K(t)]^T$$

$$b(t)=[b_1(t), \ldots, b_K(t)]^T$$

Furthermore, let K in-phase and quadrature harmonics signals be expressed by the row vectors $$I(t)=[\cos(\phi(t)), \ldots, \cos(K\phi(t))]$$

$$Q(t)=[\sin(\phi(t)), \ldots, \sin(K\phi(t))].$$

Assume the ECG signal is S(t), the difference between ECG signal and modeled shape function was provided by $$e(t)=S(t)-\hat{S}_{CPR}(t)$$

We denote the matrix regarding the step size for updating the coefficient in each harmonic component as $$U = \begin{bmatrix} \mu_1 & \cdots & 0 \\ 0 & \ddots & 0 \\ 0 & \cdots & \mu_k \end{bmatrix} = \begin{bmatrix} \mu_0 & \cdots & 0 \\ 0 & \ddots & 0 \\ 0 & \cdots & \mu_k/K \end{bmatrix}$$

where $\mu_0=0.007$

The training equations of the filter coefficient in LMS algorithm for each chest compression cycle were provided by $$a(t+1)=a(t)+2e(t)UI^T(t)$$

$$b(t+1)=b(t)+2e(t)UQ^T(t)$$

wherein the initial value of the coefficients, i.e. a(0) and b(0), were all zero.

In our LMS model, we consider five harmonic components, i.e. K=5 in Eq. (S2). In addition, when $f_0(n)>10$ Hz, we set K=1 in the model because other higher harmonics would be significantly influenced by the VF components. After training the coefficients for a compression cycle, the coefficients were converged and were used for model the associated compression signal. However, because the shape function was modeled cycle by cycle, discontinuity between consecutive compression cycles might occur. Here, the discontinuity was remedied by the average of upper and lower spline constructed by adjacent points near the discontinuity.

After the shape function was modeled by LMS algorithm in cycle-wise manner to obtain a compression signal, the VF signal was obtained by subtracting the compression signal from the ECG signal in the signal processing unit 50 (step S270). The VF signal estimated in this embodiment which resembled the actual VF signal. Finally, the signal outputting unit 50 may be configured to output the VF signal, which is not limited herein.

The present invention provides a method and system for extracting a VF signal in Electrocardiography to resolve the problems of mode mixing and mode splitting. The conjugate function is added to a non-linear and non-stationary signal for correcting a value of particular frequency function, then calculating the sum of IMFs and dividing by a number of the shadowing signal. The present invention improves analysis ability in signal and can be demonstrated in residual noise analysis. The residual noise for the UPEMD-ensemble method is significantly reduced.

Although the present invention has been described in terms of specific exemplary embodiments and examples, it will be appreciated that the embodiments disclosed herein are for illustrative purposes modifications and alterations might be made by those skilled in the art without departing from the spirit and scope of the invention as set forth in the following claims.

What is claimed is:
1. A computer-implemented method for extracting a Ventricular fibrillation (VF) signal in Electrocardiography (ECG), the method comprising:
    (A) receiving an ECG signal;
    (B) adding a plurality of shadowing functions to the ECG signal, to obtain a plurality of modification signals, wherein each pair of shadowing functions is conjugate and has same phase difference;
    (C) decomposing the plurality of modification signals by using an Empirical Mode Decomposition (EMD) method, to generate a plurality of Intrinsic Mode Functions (IMFs);

(D) calculating the sum of IMFs in different frequency regions based on time sequence, dividing by a number of the shadowing signal, to obtain a plurality of modification intrinsic mode functions;

(E) combining the plurality of modification IMFs with the same property, to obtain a shape function;

(F) modeling the shape function, to obtain a compression signal; and (G) subtracting the compression signal from the ECG signal based on time sequence, to obtain the VF signal.

2. The method according to claim 1, wherein the ECG signal is a function of amplitude and time.

3. The method according to claim 1, the steps further comprises:

(B1) adding a first shadowing signal to the ECG signal, to obtain a first modification signal;

(B2) generating a plurality of first intrinsic mode functions by using the EMD method, wherein the first intrinsic mode function is an amplitude expression of the first modification signal in the different frequency regions;

(B3) adding a second shadowing signal to the ECG signal to obtain a second modification signal;

(B4) generating a plurality of second intrinsic mode functions by using the EMD method, wherein the second intrinsic mode function is an amplitude expression of the second modification signal in the different frequency regions; and (B5) repeating to add a np-1 shadowing signal and a np shadowing signal to the ECG signal, to obtain the plurality of intrinsic mode functions, wherein the phase difference of the shadowing signals are constant.

4. The method according to claim 3, wherein the first shadowing function and the second shadowing function are conjugate.

5. The method according to claim 1, the steps further comprises:

(C1) selecting the intrinsic mode functions corresponding to a first frequency region, calculating the sum of the intrinsic mode functions based on the time sequence, then dividing by the a number of the shadowing signal, to obtain a first modification intrinsic mode function; and (C2) repeating step C1 until to obtain the modification intrinsic mode functions from all frequency regions.

6. The method according to claim 3, wherein a function of the shadowing signal is calculated according to the following expression:

$$w_i(t)=\epsilon^*\cos(2\pi t/T_w - 2\pi i/np)$$

wherein c is the amplitude of the shadowing signal, $T_w$ is a period of the shadowing signal, np is the number of the shadowing signal and i is any number into 0 to np-1.

7. The method according to claim 1, the steps further comprises:

(B1) adding a first-level of first shadowing signal to the ECG signal to obtain a first-level of first modification signal, and generating a plurality of first-level of first intrinsic mode functions by using the EMD method, wherein the first-level of first intrinsic mode function is an expression amplitude of the first-level of first modification signal in the first frequency region;

(B2) adding a first-level of second shadowing signal to the ECG signal to obtain a first-level of second modification signal, and generating a plurality of first-level of second intrinsic mode functions by using the EMD method, wherein the first-level of second intrinsic mode function is an expression amplitude of the first-level of second modification signal in the first frequency region;

(B3) repeating step B1 to B2 to add a first level of np-1 shadowing signal and a first level of np shadowing signal to the ECG signal, to obtain the plurality of first level intrinsic mode functions, wherein the phase difference of the shadowing signals are constant;

(B4) calculating the sum of the first level intrinsic mode functions based on the time sequence, then dividing by the number of shadowing signal, to obtain a first modification intrinsic mode function; and (B5) repeating step B1 to B4 to add a m level of shadowing signal to the ECG signal, to obtain a plurality of m level of intrinsic mode functions, calculating the sum of m level of the intrinsic mode functions based on the time sequence, then dividing by the number of shadowing signal to obtain a first level of m modification intrinsic mode function, until to obtain the modification intrinsic mode functions from all frequency regions.

8. The method according to claim 7, wherein a m level of function of the shadowing signal is calculated according to the following expression:

$$w_i(t)=\epsilon^*\cos(2\pi t/2^m - 2\pi i/np)$$

wherein the np-1 shadowing signal and the np shadowing signal is a m level of the shadowing function, wherein m is corresponding to the m level of the modification intrinsic mode function.

9. A system for extracting a VF signal in ECG comprising:
a signal collecting unit, to receive an ECG signal;
a signal processing unit electrically connected to the signal collecting unit, to add a plurality of shadowing functions to the ECG signal, to obtain a plurality of modification signals, wherein each pair of shadowing functions is conjugate and has same phase difference, then decomposing the plurality of modification signals by using an Empirical Mode Decomposition (EMD) method, to generate a plurality of Intrinsic Mode Functions (IMFs), calculating the sum of IMFs in different frequency regions based on time sequence, dividing by a number of the shadowing signal, to obtain a plurality of modification intrinsic mode functions, combining the plurality of modification IMFs with the same property, to obtain a shape function, modeling the shape functions to obtain a compression signal, and subtracting the compression signal from the ECG signal based on time sequence to obtain the VF signal; and
a signal outputting unit connected to the signal processing unit, to output the VF signal.

10. The system according to claim 9, wherein the ECG signal is a function of amplitude and time.

* * * * *